United States Patent [19]

Oda et al.

[11] Patent Number: 5,128,350
[45] Date of Patent: Jul. 7, 1992

[54] PYRAZOLYL ACRYLIC ACID DERIVATIVES AND AGRICULTURAL/HORTICULTURAL FUNGICIDES CONTAINING SAID DERIVATIVES

[75] Inventors: Masatsugu Oda; Toyohiko Shike, both of Yokohama; Yumiko Miura, Meguro; Kazuhiko Kikutake; Mana Sekine, both of Yokohama, all of Japan

[73] Assignee: Mitsubishi Kasei Corporation, Tokyo, Japan

[21] Appl. No.: 780,303

[22] Filed: Oct. 22, 1991

[30] Foreign Application Priority Data

Oct. 31, 1990 [JP] Japan .................. 2-294843
Mar. 29, 1991 [JP] Japan .................. 3-66701

[51] Int. Cl.$^5$ .................. A01N 43/40; A01N 43/56; C07D 231/18; C07D 401/12
[52] U.S. Cl. .................. 514/341; 514/369; 514/407; 546/279; 548/188; 548/374; 548/377
[58] Field of Search .......... 546/279; 548/188, 374, 548/377; 514/341, 369, 407

[56] References Cited
U.S. PATENT DOCUMENTS 5,055,477  10/1991  Oda et al. .................. 548/377

Primary Examiner—Robert W. Ramsuer
Attorney, Agent, or Firm—Wenderoth, Lind & Ponack

[57] ABSTRACT

A pyrazolyl acrylic acid derivative of formula (I):

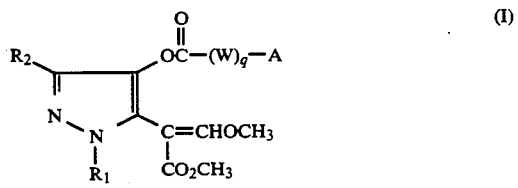

wherein $R_1$ and $R_2$ are independently hydrogen or $C_1$-$C_5$ alkyl; W is $C_1$-$C_4$ alkylene optionally substituted by $C_1$-$C_4$ alkyl, $C_2$-$C_4$ alkenylene optionally substituted by $C_1$-$C_4$ alkyl, $C_2$-$C_4$ alkynylene, —O—, —S—, or —NH—; q is 0 or 1; A is optionally substituted $C_3$-$C_7$ cycloalkyl, optionally substituted $C_6$-$C_{12}$ aryl, or optionally substituted heteroaryl having one to three heteroatoms selected from oxygen, sulfur, and nitrogen, and having two to thirteen carbon atoms in total.

Process for preparing the derivative of formula (I) and agricultural/horticultural fungicide formulation containing the derivative are also provided.

7 Claims, No Drawings

PYRAZOLYL ACRYLIC ACID DERIVATIVES AND AGRICULTURAL/HORTICULTURAL FUNGICIDES CONTAINING SAID DERIVATIVES

This invention relates to new pyrazolyl acrylic acid derivatives and intermediates thereto. The present invention also relates to agricultural/horticultural fungicides which contain at least one of said derivatives as an active ingredient.

It has been recognized that a class of acrylic acid derivatives have biological activities including fungicidal activities. Among them, a compound of the formula:

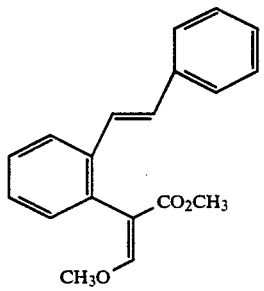

is described in European Patent Publication No. 178826, and compounds of the formulae:

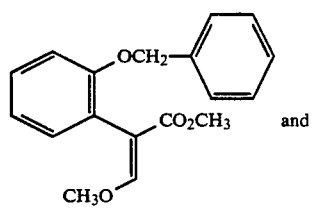

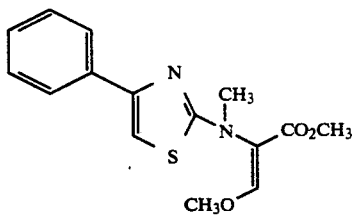

are described in Japanese Patent Publications (Kokai) Nos. 77652/1986 and 254669/1989, respectively. However, as will be apparent from the examples hereinafter discussed, these existing compounds are not always sufficiently effective in terms of fungicidal and systemic activity when used as agricultural/horticultural fungicides.

It has now been found that a class of pyrazolyl acrylic acid derivatives having a certain peculiar structure have a potent fungicidal activity as well as an excellent systemic activity for plants.

Thus, the present invention provides a pyrazolyl acrylic acid derivative of formula (I):

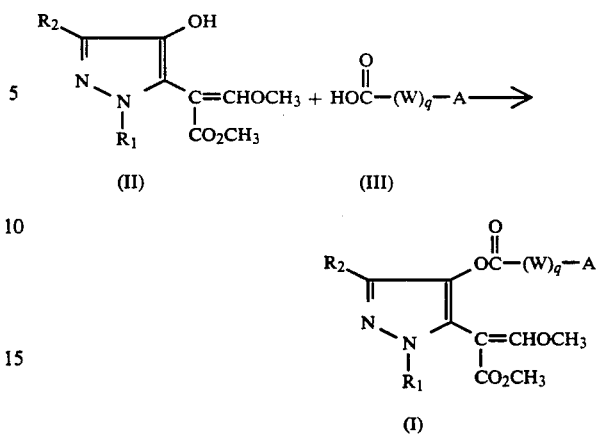

wherein $R_1$ and $R_2$ are independently hydrogen or $C_1$–$C_5$ alkyl; W is $C_1$–$C_4$ alkylene optionally substituted by $C_1$–$C_4$ alkyl, $C_2$–$C_4$ alkenylene optionally substituted by $C_1$–$C_4$ alkyl, $C_2$–$C_4$ alkynylene, —O—, —S—, or —NH—; q is 0 or 1; A is optionally substituted $C_3$–$C_7$ cycloalkyl, optionally substituted $C_6$–$C_{12}$ aryl, or optionally substituted heteroaryl having one to three heteroatoms selected from oxygen, sulfur, and, nitrogen, and having two to thirteen carbon atoms in total.

The present invention also provides a pyrazole derivative of formula (II):

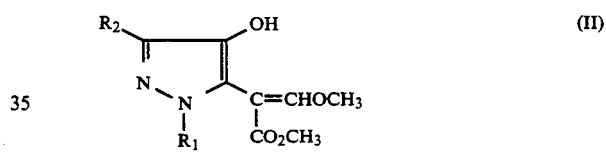

wherein $R_1$ and $R_2$ are independently hydrogen or $C_1$–$C_5$ alkyl, which is useful as an intermediate for preparing the compound of formula (I), as well as processes for preparing the compounds of the formulae (I) and (II) as hereinafter described in detail.

The present invention further provides agriculturally- and horticulturally- useful fungicidal compositions comprising, as an active ingredient, a compound of formula (I) and agriculturally-acceptable inert carrier therefor.

Pyrazolyl acrylic acid derivatives of the invention are represented by the formula (I) above. In the above formula (I), $R_1$ and $R_2$ independently represent hydrogen, or $C_1$–$C_5$ alkyl such as methyl, ethyl, n-propyl, isopropyl, n-butyl, t-butyl, n-pentyl, and the like. $R_1$ is preferably hydrogen or $C_1$–$C_4$ alkyl, and more preferably methyl or ethyl, and $R_2$ is preferably hydrogen or $C_1$–$C_3$ alkyl, and more preferably methyl, ethyl or propyl.

The symbol W represents $C_1$–$C_4$ alkylene optionally substituted by $C_1$–$C_4$ alkyl, such as methylene, methylmethylene, dimethylmethylene, ethylmethylene, ethylene, ethylethylene, or trimethylene; $C_2$–$C_4$ alkenylene optionally substituted by $C_1$–$C_4$ alkyl, such as vinylene, methylvinylene, or propenylene; $C_2$–$C_4$ alkynylene such as ehtynylene or propynylene; —O—; —S—; or —NH—. Preferred W is methylene, ethylene, vinylene, —O—, —S—, or —NH—. q represents 0 or 1.

The symbol A represents $C_6$–$C_{12}$ aryl such as phenyl, xylyl, or naphthyl; heteroaryl having one to three heteroatoms selected from oxygen, sulfur, or nitrogen, and having two to thirteen carbon atoms, such as thiazolyl, benzothiazolyl, pyridyl, thienyl, furyl, pyrazolyl, or pyrimidyl; or $C_3$-$C_7$ cycloalkyl such as cyclopropyl, cyclobutyl, or cyclohexyl. These groups may have one or more substituents.

Preferably, A represents

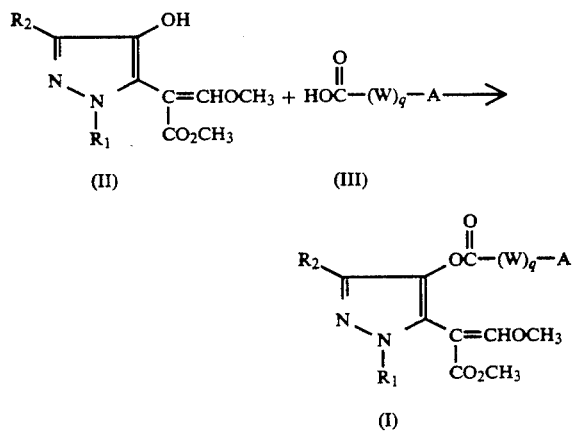

or above-noted cycloalkyl substituted by $(X)_r$, wherein X is $C_1$-$C_{10}$ alkyl such as methyl, ethyl, propyl, isopropyl, n-butyl, isobutyl, sec-butyl, tert-butyl, n-pentyl, n-hexyl, n-heptyl, n-octyl, n-nonyl, and n-decyl; $C_2$-$C_{11}$ alkenyl such as vinyl, allyl, 1-propenyl, 2-butenyl, 1,3-butadienyl, 2-pentenyl, 2-hexenyl, 2-heptenyl, 2-octenyl, 2-nonenyl, 2-decenyl, and 2-undecenyl; Cl-C10 alkoxy such as methoxy, ethoxy, n-propoxy, isopropoxy, n-butoxy, isobutoxy, sec-butoxy, tert-butoxy, n-pentyloxy, n-hexyloxy, n-heptyloxy, n-octyloxy, n-nonyloxy, and n-decyloxy; $C_1$-$C_{10}$ alkylthio such as methylthio, ethylthio, n-propylthio, isopropylthio, n-butylthio, isobutylthio, sec-butylthio, tert-butylthio, n-pentylthio, n-hexylthio, n-heptylthio, n-octylthio, n-nonylthio, and n-decylthio; $C_2$-$C_{11}$ alkenyloxy such as vinyloxy, allyloxy, 1-propenyloxy, 2-butenyloxy, 1,3-butadienyloxy, 2-pentenyloxy, 2-hexenyloxy, 2-heptenyloxy, 2-octenyloxy, 2-nonenyloxy, 2-decenyloxy, and 2-undecenyloxy; $C_2$-$C_{11}$ alkynyloxy such as ethynyloxy, propargyloxy, 1-propynyloxy, 2-butynyloxy, 2-pentynyloxy, 2-hexynyloxy, 2-heptynyloxy, 2-octynyloxy, 2-nonynyloxy, 2-decynyloxy, and 2-undecynyloxy; $C_2$-$C_{11}$ alkylcarbonyl such as acetyl, propionyl, butyryl, isobutyryl, valeryl, isovaleryl, pivaloyl, hexanoyl, heptanoyl, octanoyl, nonanoyl, decanoyl, and undecanoyl; $C_2$-$C_{11}$ alkylcarbonyloxy such as acetoxy, propionyloxy, butyryloxy, isobutyryloxy, valeryloxy, isovaleryloxy, pivaloyloxy, hexanoyloxy, heptanoyloxy, octanoyloxy, nonanoyloxy, decanoyloxy, and undecanoyloxy; $C_7$-$C_{13}$ arylcarbonyl such as benzoyl, toluoyl, and naphthoyl; $C_4$-$C_9$ cycloalkylcarbonyloxy such as cyclobutylcarbonyloxy, cyclopentylcarbonyloxy, cyclohexylcarbonyloxy, cycloheptylcarbonyloxy, cyclooctylcarbonyloxy, and cyclononylcarbonyloxy; $C_7$-$C_{13}$ arylcarbonyloxy such as benzoyloxy, toluoyloxy, and naphthoyloxy; $C_6$-$C_{12}$ aryl such as phenyl, tolyl, xylyl, and naphthyl; $C_6$-$C_{12}$ aryloxy such as phenoxy, tolyloxy, xylyloxy, and naphthyloxy; heteroaryl having one to three heteroatoms selected from oxygen, sulfur, and nitrogen, and having two to thirteen carbon atoms, such as thienyl, benzothienyl, thianthrenyl, furyl, isobenzofuryl, benzofuryl, phenoxathynyl, pyrrolyl, imidazolyl, pyrazolyl, pyridyl, pyrazinyl, pyrimidinyl, pyridazinyl, indolizinyl, isoindolyl, indolyl, isoquinolyl, quinolyl, phthalazinyl, naphthylzinyl, quinoxylinyl, quinazolinyl, cinnolinyl, carbazolyl, phenanthridinyl, acridinyl, phenanthrolinyl, phenazinyl, isothiazolyl, thiazolyl, isooxazolyl, oxazolyl, and furazanyl; heteroaryloxy having one to three heteroatoms selected from oxygen, sulfur, and nitrogen, and having two to thirteen carbon atoms, such as thienyloxy, benzothienyloxy, thianthrenyloxy, furyloxy, isobenzofuryloxy, benzofuryloxy, phenoxathynyloxy, pyrrolyloxy, imidazolyloxy, pyrazolyloxy, pyridyloxy, pyrazinyloxy, pyrimidinyloxy, pyridazinyloxy, indolizinyloxy, isoindolyloxy, indolyloxy, isoquinolyloxy, quinolyloxy, phthalozinyloxy, naphthylzinyloxy, quinoxylinyloxy, quinazolinyloxy, cinnolinyloxy, carbazolyloxy, phenanthridinyl, acridinyloxy, phenanthrolinyloxy, phenazinyloxy, isothiazolyloxy, thiazolyloxy, isooxazolyloxy, oxazolyloxy, and furazanyloxy; $C_7$-$C_{12}$ aralkyl such as benzyl, phenethyl, phenylpropyl, naphthylmethyl, and naphthylethyl; $C_2$-$C_7$ aralkyloxy such as benzyloxy, phenethyloxy, phenylpropyloxy, naphthylmethyloxy, and naphthylethyloxy; hydrogen; halogen such as fluoro, chloro, bromo, and iodo; cyano; or nitro.

The above-noted $C_1$-$C_{10}$ alkyl, $C_2$-$C_{11}$ alkenyl, $C_1$-$C_{10}$ alkoxy, $C_1$-$C_{10}$ alkylthio, $C_2$-$C_{11}$ alkenyloxy, $C_2$-$C_{11}$ alkynyloxy, $C_2$-$C_{11}$ alkylcarbonyl, and $C_2$-$C_{11}$ alkylcarbonyloxy may be substituted by one or more substituents selected from $C_1$-$C_5$ alkoxy, halogen, nitro, cyano, and trifluoromethyl, and the $C_7$-$C_{13}$ arylcarbonyl, $C_4$-$C_9$ cycloalkylcarbonyloxy, $C_7$-$C_{13}$ arylcarbonyloxy, $C_6$-$C_{12}$ aryl, $C_6$-$C_{12}$ aryloxy, heteroaryl, heteroaryloxy, $C_7$-$C_{12}$ aralkyl, and $C_7$-$C_{12}$ aralkyloxy may be substituted by one or more substituents selected from $C_1$-$C_5$ alkyl, $C_1$-$C_5$ alkoxy, halogen, nitro, cyano, and trifluoromethyl.

X preferably represents $C_1$-$C_4$ alkyl, $C_2$-$C_3$ alkenyl, $C_1$-$C_3$ alkoxy, $C_1$-$C_3$ alkylthio, $C_2$-$C_3$ alkenyloxy, $C_2$-$C_3$ alkynyloxy, or $C_2$-$C_5$ alkylcarbonyloxy, each optionally substituted by halogen; hydrogen; halogen; cyano; nitro; or phenyl, phenoxy, benzyl, benzyloxy, thiazolyl, thiazolyloxy, pyridyloxy, benzoyl, or benzothiazolyl, each optionally substituted by one or more substituents selected from $C_1$-$C_4$ alkyl, $C_1$-$C_4$ alkoxy, halogen, nitro, cyano, and trifluoromethyl; provided that adjacent two Xs may form a ring so that A may represent 2,3-dihydrobenzofuran, chroman, naphthalene, fluorene, anthraquinone, or benzo-1,3-diol.

More preferably, X represents methyl, ethyl, isopropyl, or tert-butyl, each optionally substituted; methoxy, ethoxy, or propoxy optionally substituted; methylthio optionally substituted; vinyl optionally substituted; phenyl optionally substituted; phenoxy optionally substituted; benzyl optionally substituted; benzyloxy; pyridyloxy optionally substituted; hydrogen; fluoro, chloro, bromo; cyano; or nitro, wherein the substituents for the above-noted methyl, methoxy, propoxy, methylthio, and vinyl groups include fluoro and chloro, and the substituents for the above-noted phenyl, phenoxy, benzyl, and pyridyloxy include methyl, butyl, methoxy, fluoro, chloro, nitro, cyano, and trifluoromethyl, Two adjacent Xs may form a fused ring together with A. Examples of such fused ring are 2,3-dihydrobenzofuran, chroman, naphthalene, fluorene, anthraquinone, benzo-1,3-diol, with 2,3-dihydrobenzofuran, chroman and naphthalene being preferred.

In the formula (I), l is an integer of 1-5, preferably 1-3; m is an integer of 1-2; n is an integer of 1-3; p is an integer of 1-4, preferably 1-3; r is an integer of 1-12, preferably 1-6.

Typical examples of the compounds according to the invention represented by the formula I are shown in Table 1 below, but the compounds of this invention are on no account limited to those examples.

TABLE 1

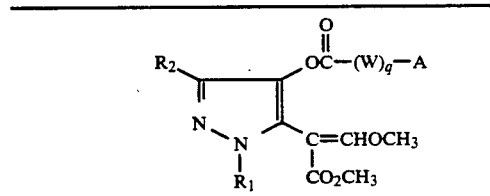

| $R_1$ | $R_2$ | $-(W)_q-A$ |
|---|---|---|
| $-CH_3$ | $-CH_3$ | (phenyl) |
| $-CH_3$ | $-CH_3$ | (3-chlorophenyl) |
| $-CH_3$ | $-CH_3$ | (4-chlorophenyl) |
| $-CH_3$ | $-CH_3$ | (3,5-dichlorophenyl) |
| $-CH_3$ | $-CH_3$ | (4-fluorophenyl) |
| $-CH_3$ | H | $-NH-$(4-methylphenyl) |
| $-C_2H_5$ | $-CH_3$ | (3-phenoxyphenyl, S-linked) |
| $-CH_3$ | $-CH_3$ | (2,3-difluoro-4,6-dichlorophenyl) |

TABLE 1-continued

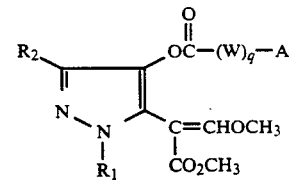

| $R_1$ | $R_2$ | $-(W)_q-A$ |
|---|---|---|
| $-CH_3$ | $-CH_3$ | (4-bromophenyl) |
| $-CH_3$ | $-CH_3$ | (3-phenoxyphenyl) |
| $-CH_3$ | $-CH_3$ | (3-phenoxy-4-fluorophenyl) |
| $-CH_3$ | $-CH_3$ | (4-phenoxyphenyl) |
| $-CH_3$ | $-CH_3$ | (3-(2-cyanophenoxy)phenyl) |
| $-CH_3$ | $-CH_3$ | (3-(2-nitrophenoxy)phenyl) |
| $-CH_3$ | H | (thienyl) |
| -iso-$C_3H_7$ | $-CH_3$ | (4-(4-trifluoromethylphenoxy)phenyl) |
| $-CH_3$ | $-CH_3$ | (3-phenoxy-4-methylphenyl) |

TABLE 1-continued
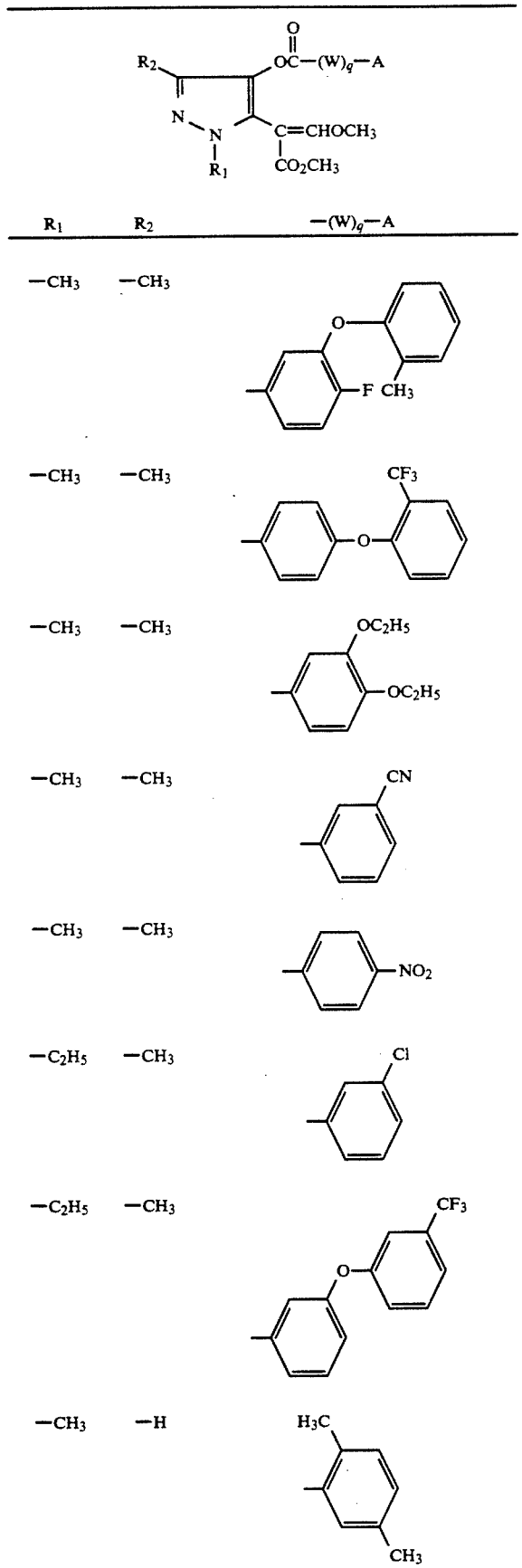
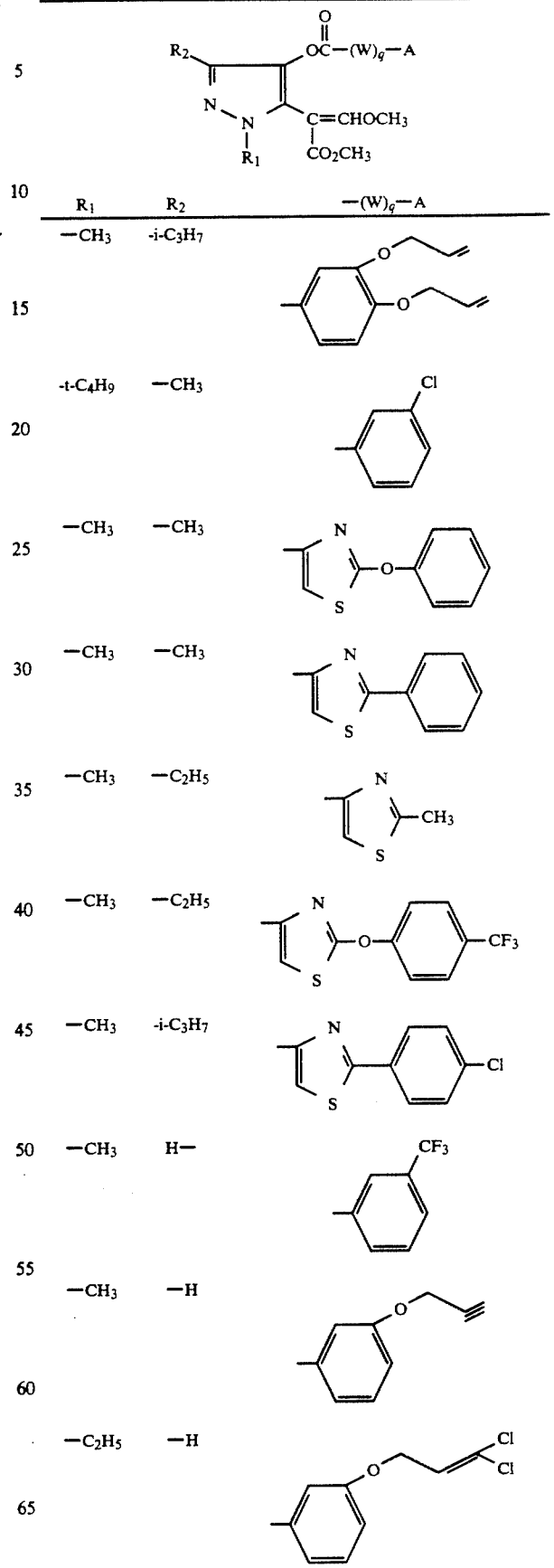

TABLE 1-continued
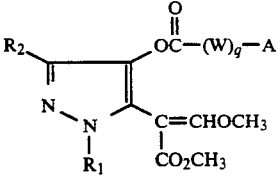
| R₁ | R₂ | —(W)_q—A |
|---|---|---|
| —CH₃ | —H | 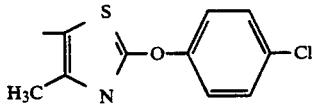 |
| —CH₃ | —CH₃ | 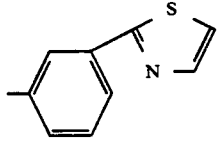 |
| —CH₃ | —CH₃ | 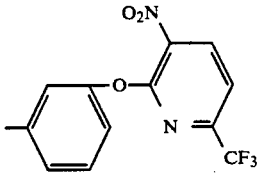 |
| —CH₃ | —CH₃ | 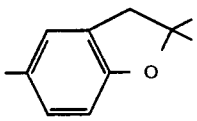 |
| —CH₃ | —CH₃ | 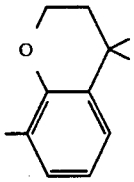 |
| —CH₃ | —CH₃ | 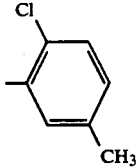 |
| —CH₃ | —CH₃ | 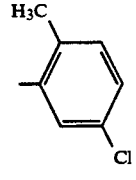 |
| —CH₃ | —CH₃ | 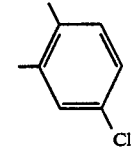 |
TABLE 1-continued
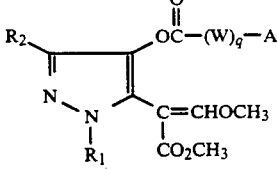
| R₁ | R₂ | —(W)_q—A |
|---|---|---|
| —CH₃ | —CH₃ | 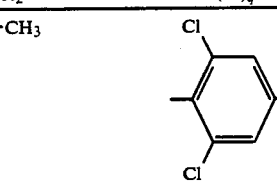 |
| —H | —CH₃ | 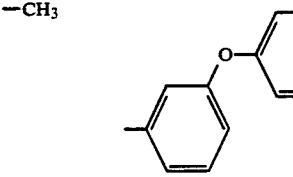 |
| —CH₃ | —C₂H₅ | 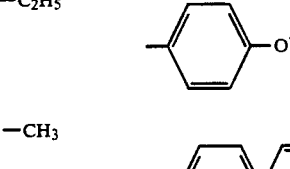 |
| —CH₃ | —CH₃ | 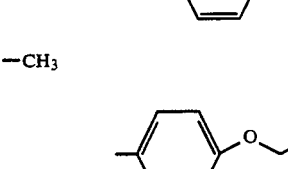 |
| —CH₃ | —CH₃ | 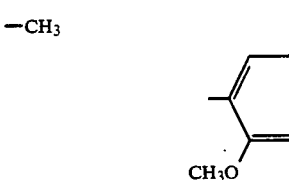 |
| —CH₃ | —CH₃ | 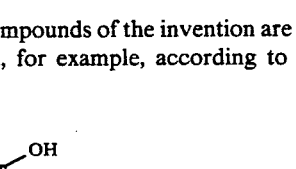 |
All the compounds of the invention are novel and can be prepared, for example, according to the following scheme:
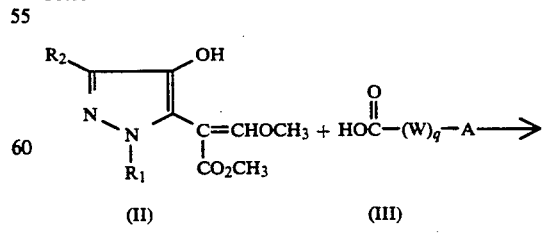

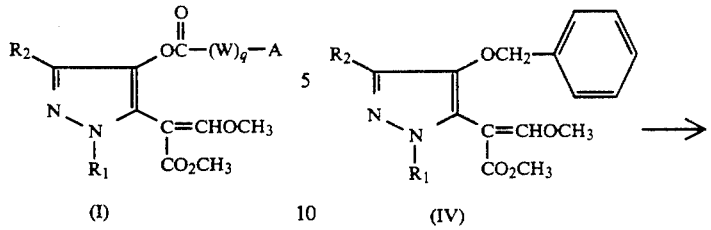

wherein R₁, R₂, W, q, and A are as defined in the above formula (I).

The compound of formula (I) is synthesized by reacting a pyrazole derivative of formula (II) with a carboxylic acid of formula (III) or a reactive derivative thereof in the presence or absence of an inert solvent.

The carboxylic acid (III) or the reactive derivative thereof is generally used in an amount of 0.5–1.5 equivalents with respect to the pyrazole derivative of formula (II). Preferred amount exists in the range of 0.9–1.1 equivalents. The reaction can be carried out at a temperature in the rage of −70° C. to the boiling point of the solvent to be used, and preferably −40° C. to the boiling point of the solvent.

Examples of the carboxylic acid (III) and the reactive derivative thereof include corresponding carboxylic acids, acid anhydrides, acid halides such as acid chlorides, and carboxylic acid esters.

Examples of the solvent which may be used in the reaction include aromatic hydrocarbons such as benzene, toluene, and the like; halogenated hydrocarbons such as carbon tetrachloride, chloroform, and the like; aromatic halogenated hydrocarbons such as chlorobenzene, and the like; ethers such as diethyl ether, tetrahydrofuran, dioxane, and the like; esters such as ethyl acetate, and the like; polar solvents such as dimethyl sulfoxide, dimethylformamide, water and the like.

In order to accelerate the reaction, appropriate reaction promoters may be used. Particular promoter to be used varies depending on the kinds of the carboxylic acid (III) or reactive derivative thereof. Examples of the promoters are dehydrating agents such as ethoxyacetylene, dicyclohexylcarbodiimide, diphosphorus pentaoxide when a carboxylic acid is used as a compound of formula (III); tertially amines such as N-methylmorpholine and triethylamine, aromatic bases such as pyridine, picoline and N,N-diethylaniline when an acid anhydride is used; tertiary amines such as triethylamine, aromatic bases such as pyridine, picoline, alkaline metal hydroxides such as sodium hydroxide and potassium hydroxide, alkaline metal hydrides such as sodium hydride, or alkaline metal alcoholates such as sodium ethylate when an acid halide is used; alkaline metal alcoholates such as sodium ethylate when a carboxylic acid ester is used. In general, these promoters are used in an amount of 0.01–2.0 equivalents depending on the pyrazole derivative of formula (II) used, and preferred amount is 0.9–1.1 equivalents.

A compound of formula (II), which is another starting material in the above reaction and the key intermediate to the compounds of the invention is prepared, for example, according to the following scheme.

wherein R₁ and R₂ are as defined in the above formula (I).

The starting material of formula (IV) for the preparation of the intermediate (II) can be prepared, for example, according to the method described in European Patent Publication No. 433899 or analogous methods.

The compound of formula (II) can be prepared by hydrogenating a compound of formula (IV) in the presence of an appropriate solvent. Examples of the solvent which may be used in the reaction include aromatic hydrocarbons such as benzene, toluene, and the like; esters such as ethyl acetate; carboxylic acids such as acetic acid, formic acid, and the like; alcohols such as methanol, ethanol, and the like; ethers such as tetrahydrofuran, dioxan, and the like; or polar solvents such as water.

In order to proceed the reaction readily, catalysts such as Pd-carbon can be used.

The reaction temperature is in the range of from 0° C. to the boiling point of the solvents, and preferably 10°–70° C.

All the compounds thus obtained are novel and have been demonstrated to express excellent plant fungicidal activity. The compounds of the invention possess outstanding characteristics essential for fungicides, that is, low phytotoxicity to plants, high activity in controlling phytopathogens and strong systemic activity. Main pathogens which can be controlled are *Phricularia oryzae* (rice blast), *Rhizoctonia solani* (sheath blight of rice), *Puccinia recondita* (leaf rusts of wheat), *Erysiphe graminis* (powdery mildew of various crops), *Botrytis cinerea* (grey mold of vegetables or fruit-trees) and *Phytophthora infestance* (late blight of various crops). Further, the compounds of the invention are low in toxicity to human being and livestock and fish as well. Thus, the present compounds have excellent fungicidal activity against various kinds of phytopathogens without serious toxicity and are extremely useful as active ingredients for agricultural/horticultural fungicides.

When a compound of the present invention is used as an agricultural fungicide, it can be used as it is without any further treatments. However, it is preferably formulated into a composition of an appropriate form by known procedures using agriculturally-acceptable inert adjuvants so that the active ingredient can disperse effectively upon application. Examples of adjuvants to be used in the present compositions are solvents, carriers, fillers and surfactants. Appropriate forms of the fungicidal compositions are., for example, emulsifiable concentrates, wettable powders and dusts.

Examples of suitable solvents include water; alcohols such as methanol, ethanol, ethylene glycol and the like; ketones such as acetone, methyl ethyl ketone, cyclohexanone and the like; ethers such as diethyl ether, dioxane, Cellosolve and the like; aliphatic hydrocarbons such as kerosene, fuel oil and the like; aromatic hydrocarbons such as benzene, toluene, xylene, solvent naphtha, methyl naphthalene and the like; hydrocarbon halides such as dichloroethane, trichlorobenzene, carbon tetrachloride and the like; acid amides such as dimethylformamide and the like; esters such as ethyl acetate, butyl acetate, glycerol esters of fatty acids and the like; nitriles such as acetonitrile and the like. The solvents may be used alone or as a mixture comprising two or more of them.

Examples of suitable fillers include clays such as kaolin, bentonite and the like; talcs such as talc, pyrophyllite and the like; mineral powders such as diatomaceous, oxides including white carbon and the like; and powders derived from plants such as soybean powder, carboxymethyl cellulose (CMC) and the like. These fillers may be used alone or as a mixture comprising two or more of them.

Surfactants which serve as spreading agents, dispersing agents, emulsifying agents or penetrating agents may be also included in the composition of the invention. Examples of surfactants include nonionic surfactants such as polyoxyethylene alkylallyl ether, polyoxyethylene sorbitan monolaurate and the like; cationic surfactants such as alkyldimethylbenzylammonium chloride, alkylpyridinium chloride and the like; anionic surfactants such as alkylbenzene sulfonate, lignosulfonate, higher alcohol sulfate and the like; amphoteric surfactants such as alkyldimethyl betaine, dodesylaminoethyl glycine and the like. These surfactants can be used alone or as a mixture comprising two or more of them.

When the compound of the invention is used in the form of emulsion, the agricultural fungicidal composition can be provided as a concentrated formulation which is diluted with water before use to give an emulsion containing the active compound at a suitable concentration for application, for example, spray application. The concentrated emulsifiable formulations generally contain about 10 to about 80 parts, preferably about 10 to about 70 parts, of the active compounds of the invention, about 10 to 90 parts, preferably about 20 to about 80 parts, of solvent and about 3 to about 20 parts, preferably about 5 to about 15 parts, of surfactants.

When the compound of the invention is used in the form of wettable powder, the composition of the invention can be provided as a mixture to be diluted with a solvent such as water before use, which mixture contains about 5 to about 80 parts, preferably about 10 to about 70 parts, of the active compound, about 10 to about 90 parts, preferably about 20 to about 80 parts, of fillers and about 1 to about 20 parts, preferably about 3 to about 15 parts, of surfactants.

When the compound of the invention is used in the form of dust, the formulation of the invention can be prepared simply by intimately mixing about 0.1 to about 10 parts, preferably about 1 to about 5 parts of the active compound with about 90 to about 99.9 parts, preferably about 95 to about 99 parts of suitable fillers such as kaolin, bentonite, talc and the like.

The composition of the invention may additionally contain other active substances such as another fungicides, insecticides, acaricides and the like, provided that they are no longer inhibitory to the fungicidal activity of the compound of the invention.

The fungicidal compositions of the present invention can be effectively applied either by spraying or dusting to plants or by application to water surface. In case of stem-foliar spray, emulsifiable concentrated formulation or wettable powder of the invention is diluted with water so as to give a emulsion or solution containing about 10 to about 1000 ppm of active compound and applied at an application rate ranging from about 0.5 to about 50 L/are (i.e., about 1 to about 20 L/are).

The following examples further illustrate the compound of the invention and the process preparing the same. The examples are not intended to be limiting to the scope of the invention in any respect and should not so construed. All the compounds prepared in the Examples were confirmed on the basis of elemental analysis, and IR and NMR spectroscopies.

PREPARATION 1

Preparation of (E)-methyl 2-(1,3-dimethyl-4-hydroxypyrazol-5-yl)-3-methoxyacrylate.

To a solution of (E)-methyl 2-(4-benzyloxy-1,3-dimethylpyrazol-5-yl)-3-methoxyacrylate (56 g, 17.7 mmol) in methanol (560 ml) was subjected to hydrogenation in the presence of 5% powdered palladium/carbon (5.3 g). When the reaction completed, the mixture was filtered and the filtrate was concentrated under reduced pressure. The residue, when recrystallized from a solvent system of methanol/ethyl acetate/n-hexane, gave a purified (E)-methyl 2-(1,3-dimethyl-4-hydroxypyrazol-5-yl)-3-methoxyacrylate (38 g, yield 94.8 %). M.p.=172.7°–173.4 ° C.

NMR (300 MHz, CDCl$_3$) δ ppm: 2.41(3H,s), 3.77(3H,s), 3.88(3H,s), 4.00(3H,s), 5.33(H,s), 7.78(H,s)

EXAMPLE 1

Preparation of (E)-methyl 2-[4-(2,4-dichlorobenzoyloxy)-1,3-dimethylpyrazol-5-yl]-3-methoxyacrylate (compound No. 7 in Table 2)

To a solution of (E)-methyl 2-(1,3-dimethyl-4-hydroxypyrazol-5-yl)-3-methoxyacrylate (obtained in the above preparation 1; 0.6 g, 2.65 mmol) and triethylamine (0.32 g, 3.17 mmol) in ethyl acetate (10 ml) was added dropwise 2,4-dichlorobenzoyl chloride (0.65 g, 3.15 mmol) under ice-cooling and the mixture was stirred at room temperature for one hour. The mixture was washed successively with water and saturated brine, dried over anhydrous sodium sulfate and concentrated. The residue, when purified by chromatography on silica gel (eluent; ethyl acetate/n-hexane =1:1) and recrystallization from ethyl acetate/n-hexane, gave (E)-methyl 2-[4-(2,4-dichlorobenzoyloxy)-1,3-dimethylpyrazol-5-yl]-3-methoxyacrylate (1.04 g; yield 99 %).

According to the procedure described in the above Example 1, compounds Nos. 1–6 and 8–71 in Table 2 were prepared.

TABLE 2
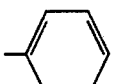
| Compd. No. | R₁ | R₂ | —(W)$_q$—A | physico-chemical property |
|---|---|---|---|---|
| 1 | —CH₃ | —CH₃ | 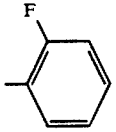 | NMR (300MHz, CDCl₃) 2.20(3H, s), 3.66(3H, s), 3.68(3H, s), 3.79(3H, s), 7.49(2H, dd), 7.60(H), 7.62(H, s), 8.15(2H, dd) |
| 2 | —CH₃ | —CH₃ | 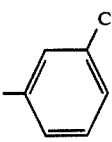 | m.p. 77.5–78° C. |
| 3 | —CH₃ | —CH₃ | 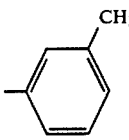 | m.p. 102–104° C. |
| 4 | —CH₃ | —CH₃ | 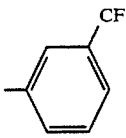 | m.p. 88.5–89° C. |
| 5 | —CH₃ | —CH₃ | 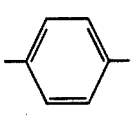 | m.p. 96.5–97.5° C. |
| 6 | —CH₃ | —CH₃ | 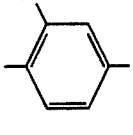 | m.p. 169–170° C. |
| 7 | —CH₃ | —CH₃ | 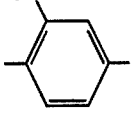 | m.p. 85.3–86° C. |
| 8 | —CH₃ | —CH₃ | 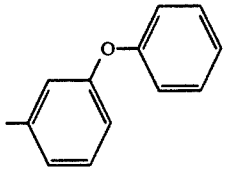 | NMR (300MHz, CDCl₃) 2.20(3H, s), 2.38(3H, s), 2.60(3H, s), 3.66(3H, s), 3.69(3H, s), 3.82(3H, s), 7.09(H, d), 7.10(H, s), 7.63(H, s), 7.96(H, d) |
| 9 | —CH₃ | —CH₃ |  | NMR (300MHz, CDCl₃) 2.19(3H, s), 3.65(3H, s), 3.67(3H, s), 3.79(3H, s), 7.03(2H), 7.15(H), 7.20(H), 7.35(2H), 7.44(H), 7.61(H), 7.76(H), 7.89(H) |

TABLE 2-continued

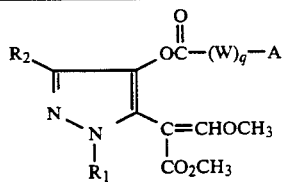

| Compd. No. | R₁ | R₂ | —(W)q—A | physico-chemical property |
|---|---|---|---|---|
| 10 | —CH₃ | —CH₃ | 2-naphthyl | m.p. 128–130° C. |
| 11 | —CH₃ | —CH₃ | 4-methyl-2-(3-chlorophenoxy)thiazol-5-yl | NMR (300MHz, CDCl₃) 2.18(3H, s), 2.64(3H, s), 3.64(3H, s), 3.70(3H, s), 3.86(3H, s), 7.2–7.4(4H), 7.64(H, s) |
| 12 | —CH₃ | —CH₃ | 5-methylthiophen-2-yl | m.p. 136.5–137° C. |
| 13 | —CH₃ | —CH₃ | 2-chloro-4-trifluoromethyl-1-(3-methylphenoxy)phenyl | m.p. 115–116° C. |
| 14 | —CH₃ | —CH₃ | 3-(3-trifluoromethylphenoxy)phenyl | m.p. 101.5–103° C. |
| 15 | —CH₃ | —CH₃ | 2-methylphenyl | m.p. 79.2–80.1° C. |
| 16 | —CH₃ | —CH₃ | 4-methylphenyl | m.p. 136.2–137.3° C. |
| 17 | —CH₃ | —CH₃ | 2-chlorophenyl | m.p. 81.4–83.4° C. |
| 18 | —CH₃ | —CH₃ | 2,4-dichlorophenyl | m.p. 73.7–75.7° C. |

TABLE 2-continued

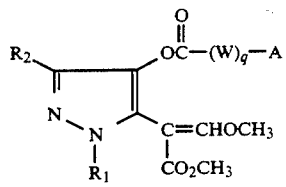

| Compd. No. | R₁ | R₂ | —(W)$_q$—A | physico-chemical property |
|---|---|---|---|---|
| 19 | —CH₃ | —CH₃ | 3-methylphenyl-O-(4-methoxyphenyl) | m.p. 80.8–81.1° C. |
| 20 | —CH₃ | —CH₃ | 2,4-dimethylphenyl | m.p. 95.4–96.5° C. |
| 21 | —CH₃ | —CH₃ | 4-tert-butylphenyl | m.p. 124.7–125.9° C. |
| 22 | —CH₃ | —CH₃ | 2-trifluoromethylphenyl | m.p. 70.9–71.8° C. |
| 23 | —CH₃ | —CH₃ | 4-trifluoromethylphenyl | m.p. 108.8–110.8° C. |
| 24 | —CH₃ | —CH₃ | (4,5-dimethylthiazol-2-yl)-O-(4-methylphenyl) | NMR (300MHz, CDCl₃) 2.16(3H, s), 2.39(3H, s), 2.64(3H, s), 3.62(3H, s), 3.68(3H, s), 3.83(3H, s), 7.14–7.26(4H, dd), 7.62(1H, s) |
| 25 | —CH₃ | —CH₃ | (4,5-dimethylthiazol-2-yl)-O-(2-methylphenyl) | NMR (300MHz, CDCl₃) 2.16(3H, s), 2.29(3H, s), 2.64(3H, s), 3.62(3H, s), 3.67(3H, s), 3.83(3H, s), 7.24–7.33(4H, m), 7.62(1H, s) |
| 26 | —CH₃ | —CH₃ | (4,5-dimethylthiazol-2-yl)-O-(4-chlorophenyl) | NMR (300MHz, CDCl₃) 2.18(3H, s), 2.63(3H, s), 3.63(2H, s), 3.69(3H, s), 3.85(3H, s), 7.25–7.43(4H, m), 7.63(1H, s) |
| 27 | —CH₃ | —CH₃ | 3-methylphenyl-O-(4-chlorophenyl) | m.p. 86.8–87.9° C. |

TABLE 2-continued

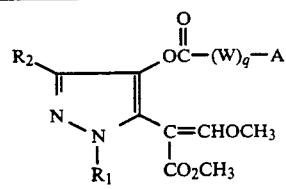

| Compd. No. | $R_1$ | $R_2$ | $-(W)_q-A$ | physico-chemical property |
|---|---|---|---|---|
| 28 | $-CH_3$ | $-CH_3$ | 3-bromo-5-methylpyridinyl | m.p. 113.1–114.7° C. |
| 29 | $-CH_3$ | $-CH_3$ | 6-chloro-2-(phenoxy)pyridinyl | m.p. 134.3–135.5° C. |
| 30 | $-CH_3$ | $-CH_3$ | 4-(4-trifluoromethylphenoxy)phenyl | m.p. 112.2–113.1° C. |
| 31 | $-CH_3$ | $-CH_3$ | 3-(4-methylphenoxy)phenyl | m.p. 88.4–89.5° C. |
| 32 | $-CH_3$ | $-CH_3$ | 2,4-bis(trifluoromethyl)phenyl | m.p. 106.3–107.7° C. |
| 33 | $-CH_3$ | $-CH_3$ | $-CH_2$-phenyl | m.p. 91–91.5° C. |
| 34 | $-CH_3$ | $-CH_3$ | $-C_2H_4$-phenyl | NMR (300MHz, $CDCl_3$) 2.05(3H, s) 2.80(2H, t) 3.02(2H, t) 3.50(3H, s) 3.61(3H, s) 3.80(3H, s) 7.15–7.25(5H, m) 7.58(1H, s) |
| 35 | $-CH_3$ | $-CH_3$ | $-CH=CH-$phenyl | m.p. 141.5–142.5° C. |
| 36 | $CH_3$ | $CH_3$ | 2-chloro-4-fluorophenyl | $CDCl_3$ 2.21(s, 3H), 3.66(s, 3H), 3.70(s, 3H) 3.87(s, 3H), 7.1(m, 1H), 7.2(dd, 1H) 7.65(s, 1H), 8.0(dd, 1H). |

TABLE 2-continued

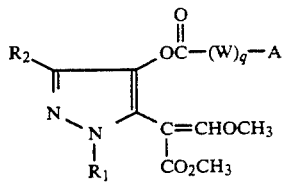

| Compd. No. | R₁ | R₂ | —(W)q—A | physico-chemical property |
|---|---|---|---|---|
| 37 | CH₃ | CH₃ | 2-F, 3-Cl phenyl | CDCl3<br>2.20(s, 3H), 3.60(s, 3H), 3.70(s, 3H), 3.86(s, 3H),<br>7.2(m, 1H), 7.6(m, 1H), 7.65(s, 1H), 7.9(m, 1H). |
| 38 | CH₃ | CH₃ | 2-CF₃, 5-F phenyl | CDCl3<br>2.20(s, 3H), 3.66(s, 3H), 3.70(s, 3H), 3.87(s, 3H),<br>7.34(ddd, 1H, J=2.7, 8.7, 9.3Hz), 7.52(dd, 1H,<br>J=2.7, 9.3Hz), 7.68(s, 1H), 7.99(dd, 1H, J=5.4, 8.7Hz). |
| 39 | CH₃ | CH₃ | 2-F, 5-CF₃ phenyl | m.p. 101.8–103.7° C. |
| 40 | CH₃ | CH₃ | 2-Cl, 5-CH₃ phenyl | CDCl3<br>2.22(s, 3H), 2.38(s, 3H), 3.67(s, 3H), 3.71(s, 3H),<br>3.88(s, 3H), 7.3(dd, 1H), 7.37(d, 1H, J=7.2Hz),<br>7.66(s, 1H), 7.7(d, 1H). |
| 41 | CH₃ | CH₃ | 2-CH₃, 5-Cl phenyl | CDCl3<br>2.20(s, 3H), 2.60(s, 3H), 3.66(s, 3H), 3.71(s, 3H),<br>3.87(s, 3H), 7.23(d, 1H, J=8.1Hz), 7.42(dd, 1H, J=2.4,<br>8.1Hz) 7.65(s, 1H), 8.01(d, 1H, J=2.4Hz). |
| 42 | CH₃ | CH₃ | 2-F, 5-CF₃ phenyl | m.p. 118.5–119.5° C. |
| 43 | CH₃ | CH₃ | 2-CH₃, 2-Cl, 2-Cl cyclopropyl | CDCl3<br>1.49(d, 1H, J=7.5Hz), 1.66(s, 3H), 2.15(s, 3H),<br>2.33(d, 1H, J=7.5Hz), 3.62(s, 3H), 3.73(s, 3H),<br>3.92(s, 3H), 7.65(s, 1H). |
| 44 | CH₃ | CH₃ | 2,3-diCl phenyl | CDCl3<br>2.22(s, 3H), 3.66(s, 3H), 3.72(s, 3H), 3.89(s, 3H),<br>7.31(dd, 1H, J=7.1, 8.1Hz), 7.65(dd, 1H, J=1.5, 8.1Hz),<br>7.67(s, 1H), 7.76(dd, 1H, J=1.5, 8.1Hz). |
| 45 | CH₃ | CH₃ | 2,3-diF phenyl | CDCl3<br>2.21(s, 3H), 3.67(s, 3H), 3.70(s, 3H), 3.86(s, 3H),<br>7.20(m, 1H), 7.41(m, 1H) 7.66(s, 1H), 7.77(m, 1H). |

TABLE 2-continued

Structure:

$$R_2\text{-pyrazole with } N-R_1, \text{ 4-position: } O-\overset{O}{C}-(W)_q-A, \text{ 5-position: } C(=CHOCH_3)(CO_2CH_3)$$

| Compd. No. | $R_1$ | $R_2$ | —(W)$_q$—A | physico-chemical property |
|---|---|---|---|---|
| 46 | CH$_3$ | CH$_3$ | 2,5-difluoro-phenyl (with methyl) | m.p. 133.4–134.5° C. |
| 47 | CH$_3$ | CH$_3$ | 2,6-dimethyl-phenyl (with methyl) | m.p. 104.7–106.9° C. |
| 48 | CH$_3$ | CH$_3$ | 2-CF$_3$, 5-CF$_3$ phenyl (with methyl) | CDCl3<br>2.22(s, 3H), 3.66(s, 3H), 3.71(s, 3H), 3.89(s, 3H), 7.69(s, 1H), 7.93(d, 1H, J=8.1Hz), 8.01(d, 1H, J=8.1Hz), 8.05(S, 1H). |
| 49 | CH$_3$ | CH$_3$ | 2-Cl, 5-Br phenyl (with methyl) | CDCl3<br>2.21(s, 3H), 3.66(s, 3H), 3.73(s, 3H), 3.89(s, 3H), 7.37(d, 1H, J=8.4Hz), 7.59(dd, 1H, J=2.4, 8.4Hz), 7.67(s, 1H), 8.06(d, 1H, J=2.4Hz). |
| 50 | CH$_3$ | CH$_3$ | 2,4-difluoro-phenyl (with methyl) | m.p. 69–71° C. |
| 51 | CH$_3$ | CH$_3$ | 2-O$_2$N, 5-Cl phenyl (with methyl) | m.p. 141.0–142.2° C. |
| 52 | CH$_3$ | CH$_3$ | 2,2-dimethyl-3-(2,2-dichlorovinyl)cyclopropyl | CDCl3<br>1.24(s, 3H), 1.33(s, 3H), 1.77(d, 1H, J=5.4Hz), 2.12(s, 3H), 2.32(dd, 1H, J=5.4, 8.4Hz), 3.62(s, 3H), 3.72(s, 3H), 3.89(s, 3H), 5.66(d, 1H, J=8.4Hz), 7.66(s, 1H). |
| 53 | CH$_3$ | CH$_3$ | 2,5-dichloro-3-methyl-thiophene | CDCl3<br>2.18(s, 3H), 3.64(s, 3H), 3.70(s, 3H), 3.86(s, 3H), 7.29(s, 1H), 7.64(s, 1H). |

TABLE 2-continued

Structure:

$$R_2\text{-pyrazole with } N-R_1, \text{ }C(=O)O-(W)_q-A \text{ at 4-position, and } C(=CHOCH_3)CO_2CH_3 \text{ at 5-position}$$

| Compd. No. | R₁ | R₂ | —(W)q—A | physico-chemical property |
|---|---|---|---|---|
| 54 | CH₃ | CH₃ | 2-methyl-4-chloro-phenoxy with CH₃O (2-methoxy-5-chloro-...) — aryl: CH₃O (ortho), Cl (para) | m.p. 106.9–107.9° C. |
| 55 | CH₃ | CH₃ | aryl: CH₃O (ortho), CH₃ (para) | CDCl3<br>2.21(s, 3H), 2.33(s, 3H), 3.65(s, 3H), 3.69(s, 3H), 3.85(s, 3H), 3.87(s, 3H), 6.9(d, 1H), 7.3(dd, 1H), 7.65(s, 1H) 7.67(d, 1H). |
| 56 | CH₃ | CH₃ | aryl: CH₃O (ortho), —O— (ortho) | CDCl3<br>2.26(3H, s) 3.63(3H, s) 3.74(3H, s) 3.87(3H, s) 3.93(3H, s) 6.90–7.05(2H, m) 7.10–7.25(2H, m) 7.71(1H, s) |
| 57 | CH₃ | CH₃ | —S—C₆H₄—CH₃ (para) | CDCl3<br>2.25(3H, s), 2.38(3H, s), 3.68(3H, s) 3.74(3H, s), 3.93(3H, s) 7.02(2H, d) 7.24(2H, d) 7.73(1H, s) |
| 58 | CH₃ | CH₃ | —NH—C₆H₄—Cl (ortho-Cl) | m.p. 132–135° C. |
| 59 | CH₃ | CH₃ | 4,5-dimethylthiazol-2-yl-O—C₆H₄—CF₃ (para) | CDCl3<br>2.18(s, 3H), 2.63(s, 6H), 3.64(s, 3H), 3.70(s, 3H), 3.87(s, 3H), 7.45(d, 2H, J=9Hz), 7.64(s, 1H), 7.72(d, 2H, J=9Hz) |
| 60 | CH₃ | CH₃ | 4,5-dimethylthiazol-2-yl-O—C₆H₄—CF₃ (meta) | CDCl3<br>2.18(s, 3H), 2.63(s, 6H), 3.64(s, 3H), 3.70(s, 3H), 3.86(s, 3H), 7.6(m, 4H) 7.64(s, 1H). |
| 61 | CH₃ | CH₃ | aryl: Cl (ortho), CH₃ (ortho), SCH₃ (para) | CDCl3<br>2.22(s, 3H), 2.52(s, 3H), 3.66(s, 3H), 3.72(s, 3H), 3.88(s, 3H), 7.32(dd, 1H, J=2.1, 8.4Hz), 7.40(d, 1H, J=8.4Hz), 7.66(s, 1H), 7.77(d, 1H, J=2.1Hz). |
| 62 | CH₃ | CH₃ | 2,4,5-trifluorophenyl | m.p. 99.1–100.4° C. |

TABLE 2-continued

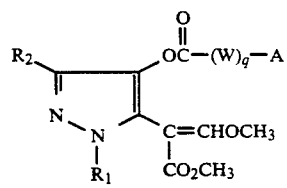

| Compd. No. | $R_1$ | $R_2$ | —$(W)_q$—A | physico-chemical property |
|---|---|---|---|---|
| 63 | $CH_3$ | H | phenyl | m.p. 93–96° C. |
| 64 | $CH_3$ | $C_2H_5$ | 4-Cl-phenyl | m.p. 121–124° C. |
| 65 | $C_2H_5$ | $CH_3$ | 4-$CH_3$-phenyl | m.p. 65–69° C. |
| 66 | $CH_3$ | $CH_3$ | 4-Cl-3-$SCCl_3$-phenyl | CDCl3<br>2.22(s, 3H), 3.66(s, 3H), 3.70(s, 3H), 3.89(s, 3H), 7.64(d, 1H, J=8.4Hz), 7.65(s, 1H), 7.89(dd, 1H, J=2.1, 8.4Hz), 8.35(d, 1H, J=2.1Hz). |
| 67 | $CH_3$ | iso-$C_3H_7$ | 4-Cl-phenyl | m.p. 57–61° C. |
| 68 | $CH_3$ | $CH_3$ | 3-$CH_3$-4-$CH(CH_3)_2$-phenyl | CDCl3<br>1.27(d, 6H, J=6.9Hz), 2.21(s, 3H), 2.59(s, 3H), 2.94(7-plet, 1H, J=6.9Hz), 3.66(s, 3H), 3.70(s, 3H), 3.84(s, 3H), 7.21(d, 1H, J=8.1Hz), 7.32(dd, 1H, J=8.1, 2.1Hz), 7.64(s, 1H), 7.89(d, 1H, J=2.1Hz). |
| 69 | $CH_3$ | $CH_3$ | 3-$CH_3$-4-Br-phenyl (with $H_3C$) | CDCl3<br>2.22(s, 3H), 2.58(s, 3H), 3.66(s, 3H), 3.72(s, 3H), 3.87(s, 3H), 7.17(d, 1H, J=8.1Hz), 7.57(dd, 1H, J=2.1, 8.1Hz), 7.65(s, 1H), 8.16(d, 1H, J=2.1Hz). |
| 70 | $CH_3$ | $CH_3$ | 2-$CH_3$-3-Br-phenyl | CDCl3<br>2.21(s, 3H), 2.69(s, 3H), 3.66(s, 3H), 3.70(s, 3H), 3.86(s, 3H), 7.14(t, 1H, J=7.8Hz), 7.66(s, 1H), 7.75(d, 1H, J=7.8Hz), 7.86(d, 1H, J=7.8Hz). |

TABLE 2-continued

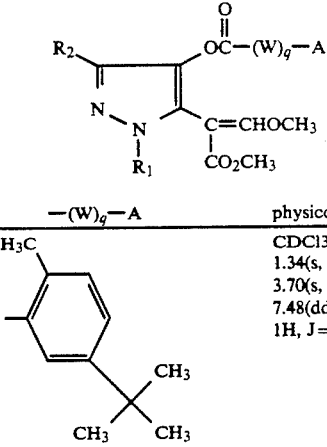

| Compd. No. | R₁ | R₂ | —(W)_q—A | physico-chemical property |
|---|---|---|---|---|
| 71 | CH₃ | CH₃ | H₃C-[3-methyl-4-(2-methyl-2-propyl... tert-butyl phenyl)] | CDCl3 1.34(s, 9H), 2.21(s, 3H), 2.58(s, 3H), 3.66(s, 3H), 3.70(s, 3H), 3.84(s, 3H), 7.22(d, 1H, J=8.1Hz), 7.48(dd, 1H, J=8.1, 2.1Hz), 7.64(s, 1H), 8.04(d, 1H, J=2.1Hz). |

The following formulation examples are illustrative only and are not intended to limit the scope of the invention in any way.

Formulation 1

A wettable powder was prepared using the following ingredients:

| | parts by weight |
|---|---|
| Active compound (No. 1 in Table 2) | 20 |
| diatomaceous earth | 75 |
| surfactant | 5 |

(principal component = alkylbenzene sulfonate).

The above ingredients are mixed and ground into a homogeneous powder.

Formulation 2

A wettable powder was prepared using the following ingredients:

| | parts by weight |
|---|---|
| Active compound (No. 10 in Table 2) | 40 |
| white carbon | 10 |
| diatomaceous earth | 47 |
| "Sorbol" 5039 | 3 |

(surfactant from TOHO Chemicals, Inc.: principal component = polyoxyethylene alkylaryl ether sulfonate).

The above ingredients are mixed and ground into a homogeneous powder.

Formulation 3

An emulsifiable concentrated formulation was prepared using the following ingredients:

| | parts by weight |
|---|---|
| Active compound (No. 5 in Table 2) | 30 |
| "Sorbol" 3005X (TOHO Chemicals, Inc.: a nonionic/anionic surfactant blend) | 15 |
| xylene | 25 |
| dimethylformamide | 30 |

The above ingredients are mixed to obtain an emulsifiable concentrated formulation.

Formulation 4

A dust was prepared using the following ingredients:

| | parts by weight |
|---|---|
| Active compound (No. 1 in Table 2) | 2 |
| N,N-kaolin clay (TSUCHIYA KAOLIN, Inc.) | 98 |

The above ingredients are intimately mixed and ground to obtain a dust.

The following experiments were conducted to determine the fungicidal efficacy of the compounds of the invention and evaluate their usefulness as an active ingredient for agricultural/horticultural fungicides.

In the experiments, the compounds of the invention are shown by the Nos. in the above Table 2, while the control compounds are shown by the symbols (A,B and C) used in the following Table 3.

TABLE 3

| Compound | chemical formula | Notes |
|---|---|---|
| A | 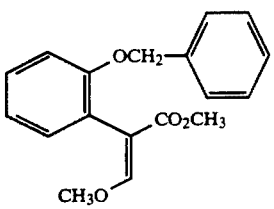 | Disclosed in Japanese Patent Publication (Kokai) No. 277652 |
| B | 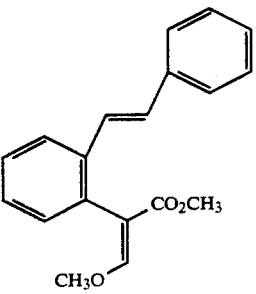 | Disclosed in European Patent Publication No. 178826 |

TABLE 3-continued

| Compound | chemical formula | Notes |
|---|---|---|
| C | [structure: phenyl-CH=CH-S-C(CH3)=N-N(CH3)-C(CO2CH3)=CH-OCH3] | Disclosed in Japanese Patent Publication (Kokai) No. 254669 |

Test 1

Evaluation of Efficacy of the Compound of the Invention on the Wheat Powdery Mildew A wettable powder containing the test compound was prepared in the same manner as previously described in the Formulation 1 and diluted with water to obtain a test solution containing the test compound at a given concentration. The test solution was then applied to a wheat (variety: Norin No. 61; 1- or 2-leaf-stage) growing in a pot (6 cm in diameter) by stem-foliar application at the application rate of 10 ml per pot. After the test solution was air-dried, the plant was inoculated with *Erysiphe graminis*. The inoculation was conducted by spraying a suspension of spores collected from leaves of wheat infected with powdery mildew. The treated plants were maintained in a green house for 7 to 10 days and the portion of diseased area on leaves of each plant was measured.

The disease control value (=prevention value) was calculated as prevention value from the equation:

Prevention value (%) = $[(U-T)/U] \times 100$ wherein U is the mean value of the percent of diseased area on untreated sections, T is the mean value of the percent of diseased area on treated sections. Results are shown in the following Table 4.

TABLE 4

| compound No. | Concentration of active ingredient (ppm) | Prevention value (%) |
|---|---|---|
| 1 | 200 | 100 |
| 2 | 200 | 95 |
| 3 | 200 | 100 |
| 4 | 200 | 95 |
| 5 | 200 | 100 |
| 6 | 200 | 100 |
| 7 | 200 | 100 |
| 8 | 200 | 97 |
| 9 | 200 | 96 |
| 11 | 200 | 98 |
| 13 | 200 | 100 |
| 15 | 200 | 100 |
| 16 | 200 | 79 |
| 17 | 200 | 90 |
| 18 | 200 | 98 |
| 20 | 200 | 100 |
| 21 | 200 | 92 |
| 22 | 200 | 100 |
| 23 | 200 | 100 |
| 24 | 200 | 68 |
| 25 | 200 | 78 |
| 28 | 200 | 100 |
| 29 | 200 | 100 |
| 32 | 200 | 100 |
| 36 | 200 | 100 |
| 37 | 200 | 96 |
| 38 | 200 | 100 |
| 39 | 200 | 99 |
| 40 | 200 | 99 |
| 41 | 200 | 99 |
| 42 | 200 | 97 |
| 43 | 200 | 98 |
| 44 | 200 | 100 |
| 45 | 200 | 99 |
| 46 | 200 | 99 |
| 47 | 200 | 99 |
| 48 | 200 | 100 |
| 49 | 200 | 99 |
| 50 | 200 | 100 |
| 52 | 200 | 70 |
| 53 | 200 | 100 |
| 55 | 200 | 82 |
| 57 | 200 | 98 |
| 58 | 200 | 93 |
| 59 | 200 | 70 |
| 60 | 200 | 92 |
| 61 | 200 | 92 |
| 62 | 200 | 100 |
| 63 | 200 | 100 |
| 64 | 200 | 95 |
| 65 | 200 | 93 |
| 68 | 200 | 100 |
| 69 | 200 | 100 |
| 70 | 200 | 100 |
| A | 200 | 0 |
| C | 200 | 12 |

Test 2

Evaluation of Efficacy of the Compound of the Invention on the Late Blight of Tomato A wettable powder containing a test compound was prepared in the same manner as previously described in the Formulation 1 and diluted with water to obtain a test solution containing the test compound at a given concentration. Three seedlings of tomato (variety : Red cherry) were grown in a plastic pot (6 cm in diameter) until 3- or 4-leaf-stage. The test solution was applied to the seedlings by stem-foliar application at the application rate of 10 ml per pot. After the test solution was air-dried, the seedlings were inoculated with *Phytophthora infestans*. The inoculation was conducted by spraying a suspension of spores formed on detached leaves of tomato. The inoculated plants were kept, at first, in a wet chamber at 20 °C for 24 hours, and then in a green house for 2 days. The portion of diseased areas of the leaves was measured. The incidence of disease was rated on the following index:

| Index | Spot area |
|---|---|
| 0 | none |
| 1 | less than ⅛ |
| 3 | ⅛ to ⅝ |
| 5 | more than ⅝ |

The incidence of disease (%) was calculated from the equation:

$$\frac{0 \times n_0 + 1 \times n_1 + 3 \times n_3 + 5 \times n_5}{5(n_0 + n_1 + n_3 + n_5)} \times 100$$

where $n_0$, $n_1$, $n_3$, and $n_5$ are the number of leaves which give the index listed above per pot.

The disease control value was calculated as percent control from the equation:

Prevention value (%) = [(U−T)/U] × 100 where U is the incidence (%) of disease on untreated sections, T is the incidence (%) of disease on treated sections. Results are shown in the following Table 5.

TABLE 5

| compound No. | Concentration of active ingredient (ppm) | Prevention value (%) |
|---|---|---|
| 1 | 200 | 72 |
| 3 | 200 | 100 |
| 4 | 200 | 88 |
| 6 | 200 | 100 |
| 7 | 200 | 100 |
| 8 | 200 | 100 |
| 9 | 200 | 100 |
| 10 | 200 | 67 |
| 11 | 200 | 100 |
| 12 | 200 | 97 |
| 13 | 200 | 100 |
| 14 | 200 | 95 |
| 15 | 200 | 100 |
| 16 | 200 | 93 |
| 17 | 200 | 95 |
| 18 | 200 | 89 |
| 19 | 200 | 96 |
| 20 | 200 | 100 |
| 21 | 200 | 79 |
| 22 | 200 | 81 |
| 23 | 200 | 99 |
| 24 | 200 | 100 |
| 25 | 200 | 100 |
| 26 | 200 | 95 |
| 27 | 200 | 98 |
| 28 | 200 | 74 |
| 29 | 200 | 100 |
| 31 | 200 | 96 |
| 32 | 200 | 89 |
| 33 | 200 | 85 |
| 35 | 200 | 92 |
| 36 | 200 | 95 |
| 37 | 200 | 95 |
| 38 | 200 | 87 |
| 39 | 200 | 99 |
| 40 | 200 | 94 |
| 41 | 200 | 100 |
| 44 | 200 | 95 |
| 45 | 200 | 90 |
| 47 | 200 | 95 |
| 49 | 200 | 100 |
| 50 | 200 | 96 |
| 51 | 200 | 100 |
| 52 | 200 | 100 |
| 53 | 200 | 100 |
| 54 | 200 | 88 |
| 56 | 200 | 100 |
| 57 | 200 | 100 |
| 58 | 200 | 95 |
| 59 | 200 | 100 |
| 60 | 200 | 100 |
| 61 | 200 | 94 |
| 62 | 200 | 64 |
| 63 | 200 | 95 |
| 64 | 200 | 90 |
| 65 | 200 | 91 |
| 67 | 200 | 95 |
| 68 | 200 | 95 |
| A | 200 | 15 |
| B | 200 | 0 |
| C | 200 | 0 |

What is claimed is:

1. A pyrazolyl acrylic acid derivative of formula (I):

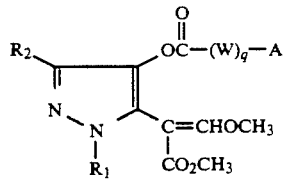

wherein $R_1$ and $R_2$ are independently hydrogen or $C_1$-$C_5$ alkyl; W is $C_1$-$C_4$ alkylene optionally substituted by $C_1$-$C_4$ alkyl, $C_2$-$C_4$ alkenylene optionally substituted by $C_1$-$C_4$ alkyl, $C_2$-$C_4$ alkynylene, —O—, —S—, or —NH—; q is 0 or 1; A is optionally substituted $C_3$-$C_7$ cycloalkyl, optionally substituted $C_6$-$C_{12}$ aryl, or optionally substituted heteroaryl having one to three heteroatoms selected from oxygen, sulfur, and nitrogen, and having two to thirteen carbon atoms in total.

2. The derivatives of claim 1 wherein A is

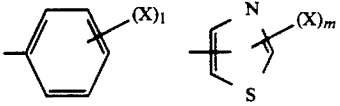

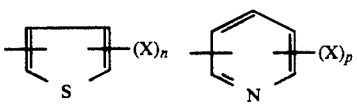

or $C_3$-$C_7$ cycloalkyl substituted by (X)r, wherein X is $C_1$-$C_{10}$ alkyl, $C_2$-$C_{11}$ alkenyl, $C_1$-$C_{10}$ alkoxy, $C_1$-$C_{10}$ alkylthio, $C_2$-$C_{11}$ alkenyloxy, $C_2$-$C_{11}$ alkynyloxy, $C_2$-$C_{11}$ alkyl carbonyl, or $C_2$-$C_{11}$ alkylcarbonyloxy, each optionally substituted by one or more substituents selected from $C_1$-$C_5$ alkoxy, halogen, nitro, cyano and trifluoromethyl; $C_7$-$C_{13}$ arylcarbonyl, $C_4$-$C_9$ cycloalkylcarbonyloxy, $C_7$-$C_{13}$ arylcarbonyloxy, $C_6$-$C_{12}$ aryl, $C_6$-$C_{12}$ aryloxy, heteroaryl having one to three heteroatoms selected from oxygen, sulfur, and nitrogen, and having two to thirteen carbon atoms, heteroaryloxy having one to three heteroatoms selected from oxygen, sulfur, and nitrogen, and having two to thirteen carbon atoms, $C_7$-$C_{12}$ aralkyl or $C_7$-$C_{12}$ aralkyloxy each optionally substituted by one or more substituents selected from $C_1$-$C_5$ alkyl, $C_1$-$C_5$ alkoxy, halogen, nitro, cyano, and trifluoromethyl; hydrogen, halogen, cyano, or nitro; and l is an integer of 1-5; m is an integer of 1-2; n is an integer of 1-3; p is an integer of 1-4; r is an integer of 1-12; provided that two Xs may form a ring so that A may represent a condensed aromatic ring or heterocycle.

3. The compound of claim 2, wherein W is methylene, ethylene, vinylene, —O—, —S—, or —N— and q is 1.

4. The compound of claim 2, wherein q is 0.

5. The compound of claim 2, wherein X is $C_1$-$C_4$ alkyl, $C_2$-$C_3$ alkenyl, $C_1$-$C_3$ alkoxy, $C_1$-$C_3$ alkylthio, $C_2$-$C_3$ alkenyloxy, $C_2$-$C_3$ alkynyloxy, or $C_2$-$C_5$ alkylcarbonyloxy, each optionally substituted by halogen; hydrogen; halogen; cyano; nitro; or phenyl, phenoxy, benzyl, benzyloxy, thiazolyl, thiazolyloxy, pyridyloxy, benzoyl, or benzothiazolyl, each optionally substituted by one or more substituents selected from $C_1$-$C_4$ alkyl, $C_1$-$C_4$ alkoxy, halogen, nitro, cyano, and trifluoromethyl; provided that adjacent two Xs may form a ring so that A may represent 2,3-dihydrobenzofuran, chroman, naphthalene, fluorene, anthraquinone, or benzo-1,3-diol.

6. The compound of claim 5, wherein X is $C_1$-$C_4$ alkyl, vinyl, $C_1$-$C_3$ alkoxy, or methylthio, each optionally substituted by halogen; hydrogen; halogen; cyano; nitro; benzyloxy; or phenyl, phenoxy, benzyl, or pyridyloxy, each optionally substituted by one or more substituents selected from $C_1$-$C_4$ alkyl, alkoxy, halogen, nitro, cyano, or trifluoromethyl; provided that adjacent two Xs may form a ring so that A may represent 2,3-dihydrobenzofuran, chroman, or naphthalene.

7. An agriculturally- and horticulturally-useful fungicidal composition comprising, as an active ingredient, a pyrazolyl acrylic acid derivative of formula (I) as defined in claim 1.

* * * * *

UNITED STATES PATENT AND TRADEMARK OFFICE
CERTIFICATE OF CORRECTION

PATENT NO. : 5,128,350

DATED : July 7, 1992

INVENTOR(S) : Masatsugu ODA et al.

It is certified that error appears in the above-identified patent and that said Letters Patent is hereby corrected as shown below:

Column 3, lines 7-24, change

"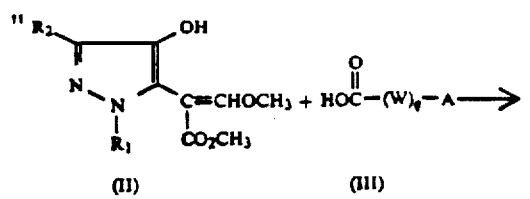

(II)          (III)

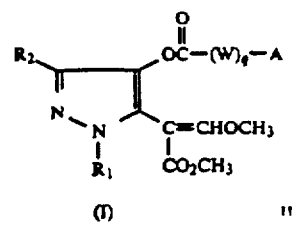

(I)          "

UNITED STATES PATENT AND TRADEMARK OFFICE
CERTIFICATE OF CORRECTION

PATENT NO.  : 5,128,350
DATED       : July 7, 1992
INVENTOR(S) : Masatsugu Oda et al Page 2 of 2

It is certified that error appears in the above-indentified patent and that said Letters Patent is hereby corrected as shown below:

to    -- 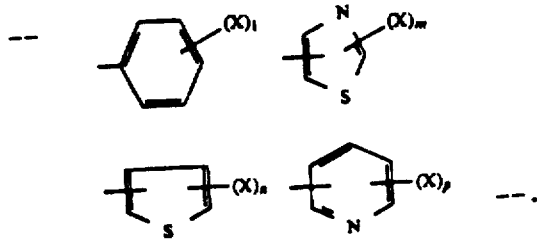 --.

Signed and Sealed this

Sixteenth Day of November, 1993

Attest:

BRUCE LEHMAN

Attesting Officer            Commissioner of Patents and Trademarks